United States Patent
Lindgren et al.

[11] Patent Number: 6,151,717
[45] Date of Patent: Nov. 28, 2000

[54] TRANSPARENT OR TRANSLUCENT EARMUFF CUP

[75] Inventors: Fredrik Lindgren, Spencer, Mass.; Brian Myers, Indianapolis, Ind.; James Hall, Lincoln, R.I.

[73] Assignee: Aearo Company, Southbridge, Mass.

[21] Appl. No.: 09/357,217

[22] Filed: Jul. 20, 1999

[51] Int. Cl.[7] .................................................. A61F 11/08
[52] U.S. Cl. ........................... 2/209; 128/867; 181/129
[58] Field of Search ............................. 2/209, 174, 423; 128/866, 867, 864; 181/129

[56] References Cited

U.S. PATENT DOCUMENTS

| | | | |
|---|---|---|---|
| 1,988,880 | 1/1935 | Strouse | 2/209 X |
| 2,570,675 | 10/1951 | Heflin | 2/174 X |
| 2,883,671 | 4/1959 | Hornickel | 2/209 |
| 4,916,758 | 4/1990 | Jordan-Ross | 2/209 X |
| 5,426,790 | 6/1995 | Robertson | 2/209 X |
| 5,551,090 | 9/1996 | Thompson | 2/209 |
| 5,749,099 | 5/1998 | Voorhees | 2/209 |

*Primary Examiner*—Peter Nerbun
*Attorney, Agent, or Firm*—Cantor Culburn LLP

[57] ABSTRACT

The present invention provides an earmuff device comprising an earmuff cup having at least a window portion which is formed of an optical material which transmits light rays in such a way that the human eye can see through the material to a degree that an earplug or other object inserted within the ear is visually perceivable to the human eye. In other words, the earmuff cup is formed of a transparent material or a translucent material so long as the earplug inserted within the wearer's ear is visually perceivable through the translucent portion of the earmuff cup. Because the earmuff cup is formed of a material that permits an individual, such as a supervisor or hearing conservationist, to perceive whether an earplug is inserted within the wearer's ear, the earmuff device of the present invention is particularly well suited for use in a dual hearing protection environment in which the previous method of compliance monitoring was time consuming and difficult.

18 Claims, 7 Drawing Sheets

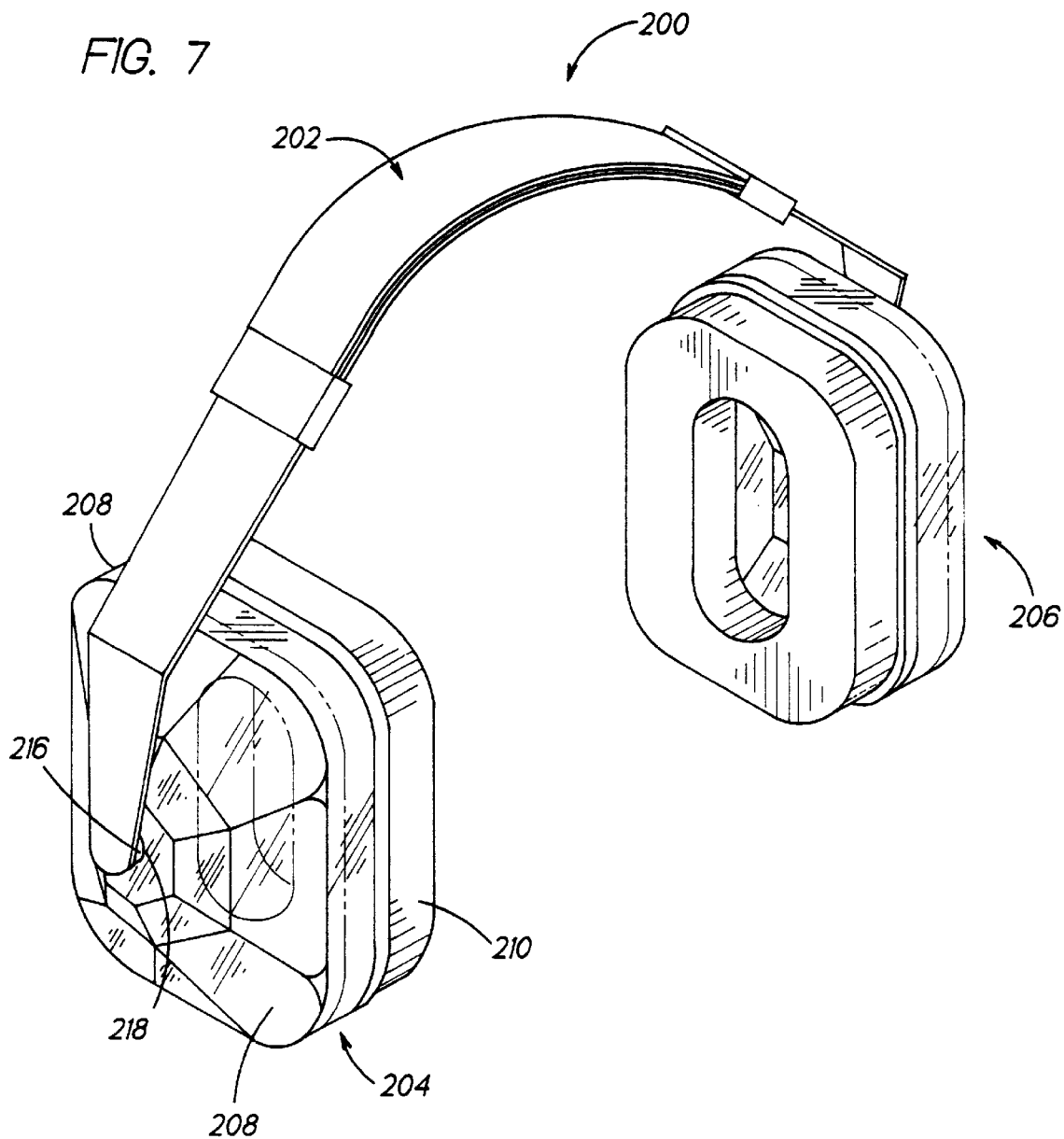

TRANSPARENT OR TRANSLUCENT EARMUFF CUP

BACKGROUND OF THE INVENTION

1. Field of the Invention

This invention relates generally to acoustic hearing protective devices and, more particularly, to an acoustical earmuff device having a pair of earmuff cup assemblies, each assembly including a rigid cup, wherein at least a portion of the rigid cup is transparent or translucent so that an earplug inserted within a wearer's ear is visually perceivable from the outside of the rigid cup.

2. Brief Discussion of the Prior Art

Environmental sounds are typically comprised of a mixture of various sound wave frequencies having varying intensities. It is well documented that repeated or prolonged exposure to sounds of sufficiently high sound pressure level will cause temporary or permanent hearing loss. For example, exposure to sound waves of some frequencies and of varying intensities under prolonged exposure can damage the auditory organ and cause serious hearing problems, including deafness. Injurious noises such as those caused by explosions or bursts are often comprised of a mixture of sound wave frequencies of varying intensity. These disturbing frequencies are in both the high and low frequency bands and have an intensity sufficient to cause hearing problems. Individuals who are frequently exposed to sound having such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

Sound attenuation devices are known which specifically address this problem. These include conventional earplugs, earmuffs, and the like which function to reduce the negative effects of exposure to dangerous frequencies by limiting the entry of all sound waves into the auditory organ. In environments where very high noise levels exist, dual hearing protection is often required. This results because if the attenuation that can be provided by a single hearing protective device is inadequate for a given noise exposure and if noise control procedures are impracticable, the one viable alternative is to use dual hearing protection. One example of dual hearing protection is an earplug used in combination with an earmuff assembly. The attenuation of the combination of these two devices is better than attenuation of either device alone and thus, dual hearing protection offers additional protection when the user is exposed to a high noise level environment.

One of the associated disadvantages of a dual hearing protective device is that people generally do not like to put objects into their ears and wear them for periods of time. For this reason and others, dual hearing protection wearers often wear the earmuff without having the pair of earplugs inserted into the ears. Consequently, the advantages offered by the dual hearing protective device are not realized and the wearer is exposed to greater levels of noise and greater risks. A wearer can wear only the earmuff without the earplugs because conventional earmuffs do not allow a supervisor or other hearing conservationist to easily enforce the use of both hearing protective devices since these individuals cannot see the earplug within each ear when the earmuff is in place surrounding the user's ears. A conventional set of acoustical earmuffs typically includes a pair of earmuff cup assemblies connected by a suitable means to a flexible headband. Each earmuff cup assembly generally consists of a rigid cup, a cushion, and optionally a sound absorbing liner. The rigid cup is formed of suitable materials and generally is formed of a relatively stiff material such as rigid polyvinyl chloride, acrylonitrile butadiene styrene (ABS) or the like. The rigid cup of the prior art are opaque in nature and thus prevent the passage of light rays through the cup material.

Accordingly, it has been found to be very difficult to enforce the use of dual hearing protection without having spot checks where the wearer is asked to remove the earmuff so that the supervisor or hearing conservationist can directly observe whether the pair of earplugs are inserted into the wearer's ears. When an individual is subjected to a spot check, the individual must discontinue working and thus productivity is lost due to the spot check. As the number of spot checks and the number of persons subjected to them increases, productivity will continue to decrease resulting in lower profitability and increasing production times. In addition, the wearer will need to at least partially remove the earmuff resulting in the wearer's ears being exposed to potentially damaging sounds. This greatly increases the chances of injury or damage to the ears. As a result, there is a need for a method and dual hearing protective device which permits the supervisor or another individual to determine whether the wearer is complying with rules, regulations, and the like by wearing the dual hearing protective device.

SUMMARY OF THE INVENTION

The above-discussed and other drawbacks and deficiencies of the prior art are overcome or alleviated by the acoustical earmuff design of the present invention, which includes a rigid cup having at least a window portion which is formed of an optical material which transmits light rays in such a way that the human eye can see through the material to a degree that an earplug or other object inserted within the ear is visually perceivable to the human eye. It is thus within the scope of the present invention that the rigid cup is formed of a transparent material or a translucent material so long as the earplug inserted within the wearer's ear is visually perceivable through the translucent portion of the rigid cup.

The rigid cup of the present invention may be entirely formed of a transparent or optically translucent material or may include only an optically transparent or translucent window which is properly positioned within the rigid cup so that an earplug inserted into the ear is visually perceivable through the window by an individual looking through the window of the rigid cup. The precise color of the rigid cup is not critical to the practice of the present invention so long as the object inserted into the ear, e.g. an inserted earplug or the like, is visually perceivable through the rigid cup. It being understood that the fine details of this object need not be discernable by the observer so long as the object itself is capable of being visually perceived. Thus, contrasting colors between the rigid cup and the earplug will increase the likelihood that the earplug can be easily discernable through the rigid cup when the wearer is wearing both.

In a preferred embodiment, the rigid cup is formed of either transparent, rigid polyvinyl chloride or acrylonitrile butadiene styrene (ABS) or translucent, rigid polyvinyl chloride or acrylonitrile butadiene styrene (ABS) so long as the translucency is such that an earplug inserted within the ear of the wearer is visually perceivable through the cup material.

Because the rigid cup is formed of a material that permits an individual, such as a supervisor or hearing conservationist, to perceive whether an earplug is inserted within the wearer's ear, the difficulties associated with the dual hearing protection monitoring process are overcome by the earmuff assembly of the present invention. Because an individual can easily perceive whether an earplug is being worn underneath the earmuff cup assembly by simply looking at the rigid cup itself, the individual can instruct and correct workers or the like that are not wearing both hearing protective devices. The present invention provides a much less complex and time consuming monitoring process because it does not require removal of the earmuff to observe whether the wearer was complying with the dual hearing protective device requirement.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES:

FIG. 7 is a perspective view of a second exemplary acoustic earmuff device according to the present invention.

DESCRIPTION OF THE PREFERRED EMBODIMENTS

Figure 1:
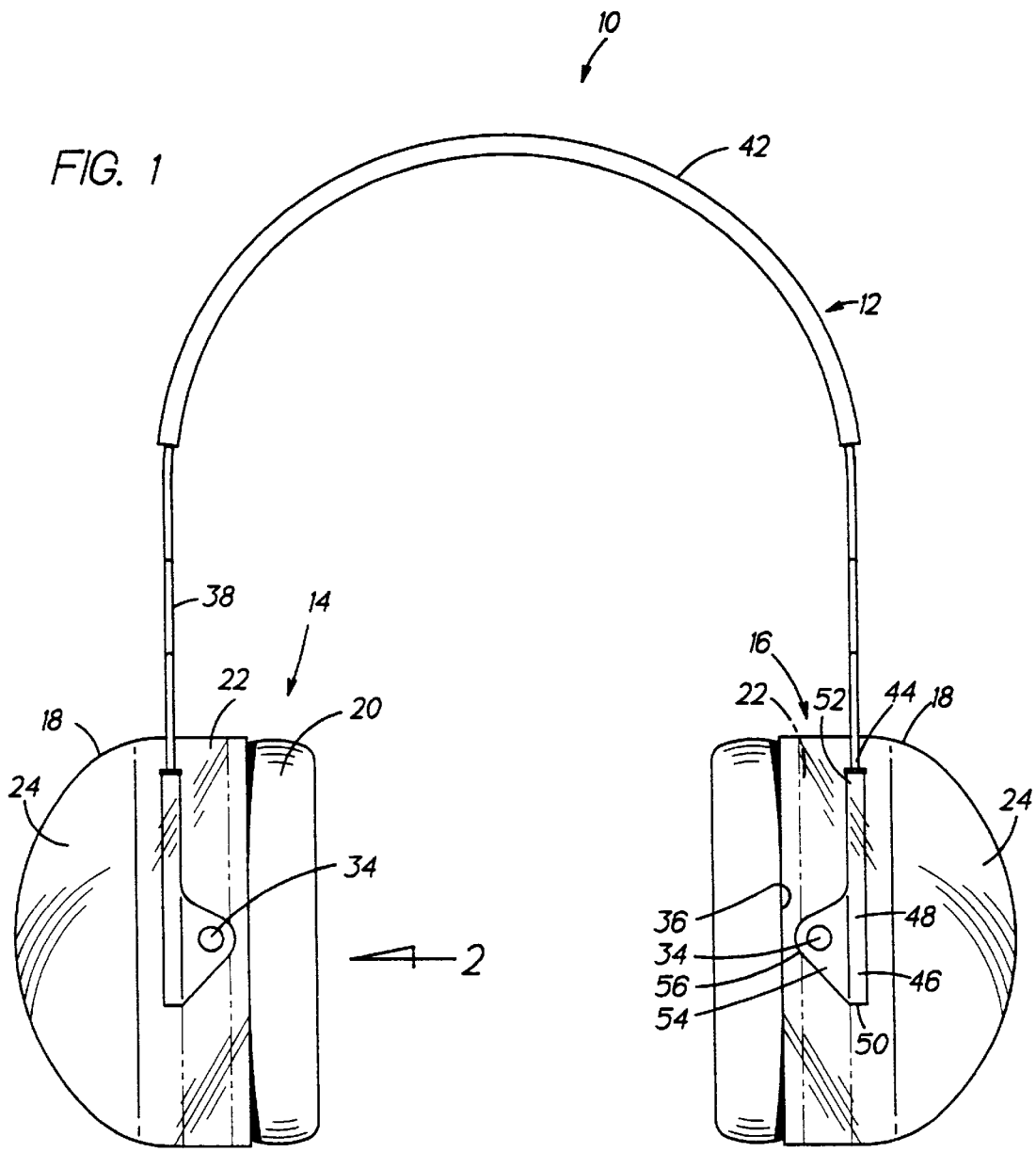
FIG. 1 is a side elevation view of an exemplary acoustic earmuff device of the present invention.

Referring now to FIGS. 1–4, an exemplary earmuff device is generally shown at 10 and broadly comprises a generally U-shaped, resilient connecting band 12 and a pair of acoustic earmuff cup assemblies 14 and 16 connected to opposite ends of connecting band 12.

Each of acoustic earmuff cup assemblies 14 and 16 comprises a rigid earcup 18, a foam cushion 20, and optionally an earmuff cup liner 22. Rigid cup 18 is generally formed of two pieces, a cup shaped portion 24 and a cushion sealplate 26, which are ultrasonically sealed together at an interface. Cup shaped portion 24 has an outer surface 30 and an inner surface 32 and in the exemplary embodiment shown in FIG. 1, cup shaped portion 24 includes a pair of spaced retaining pins 34 which extend outwardly from outer surface 30. Retaining pins 34 are preferably spaced about 180° from one another and are centrally located around a peripheral edge 36 of cup shaped portion 24. It being understood that retaining pins 34 may have a variety of cross-sectional shapes and in the exemplary embodiment shown, retaining pins 34 are generally circular in shape.

Figure 2:
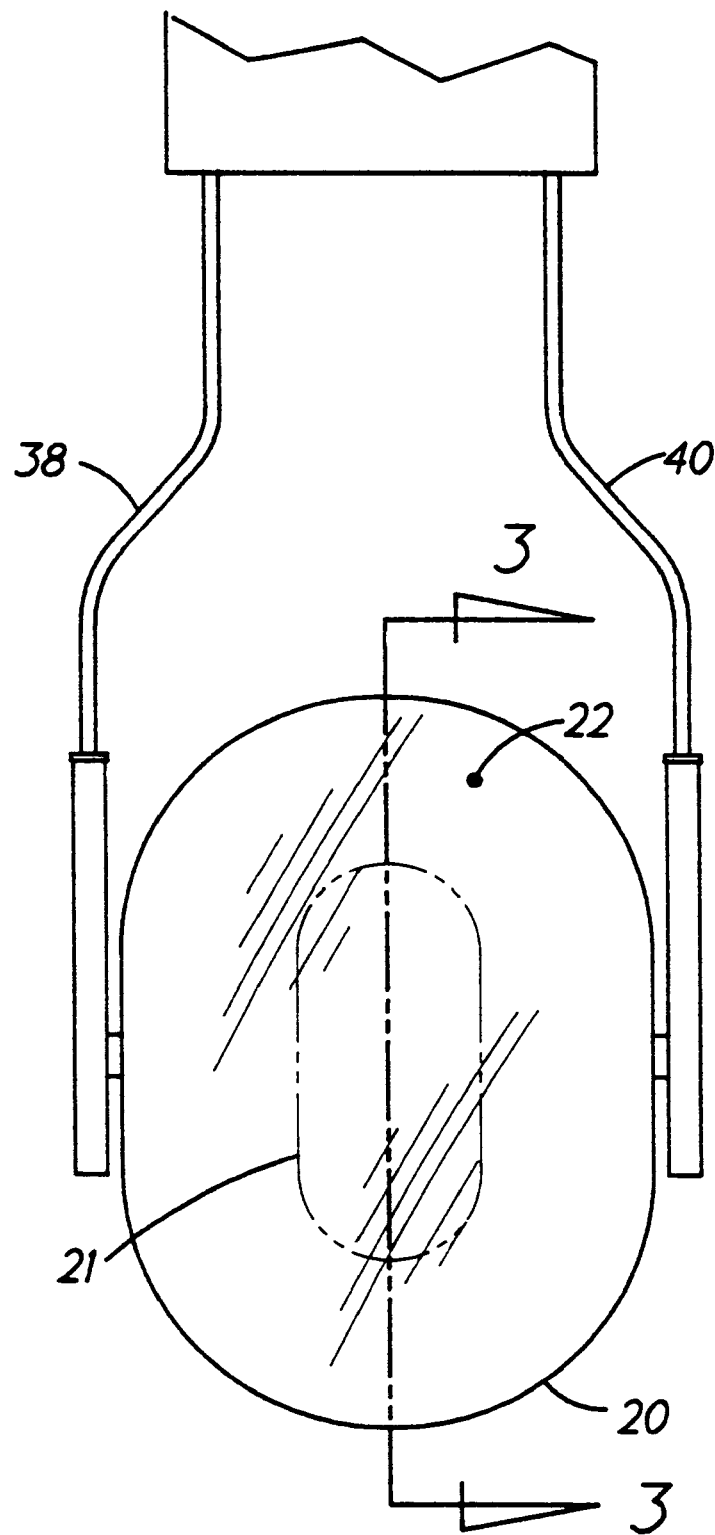
FIG. 2 is a front elevation view of the exemplary acoustic earmuff device of FIG. 1 looking in the direction of arrow 2 in FIG. 1.
Figure 3:
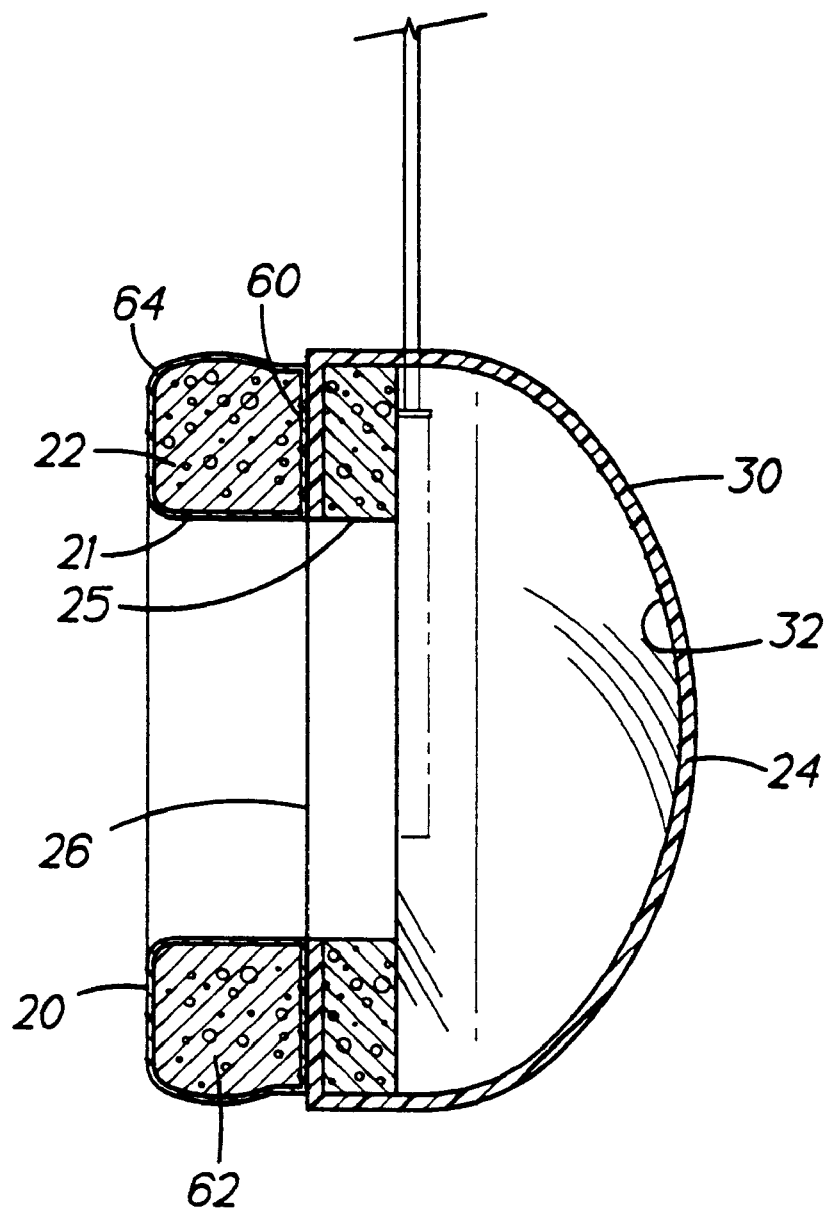
FIG. 3 is a cross-section of line 3—3 of FIG. 2.

In the exemplary embodiment shown in FIGS. 1–3, connecting band 12 comprises two generally parallel disposed, resilient wires 38 and 40 held in substantially parallel alignment by a strip 42 of flexible material, such as a rubber or a plastic. Each end 44 of resilient wires 38 and 40 includes a connector member 46 which includes a base portion 48 having a central opening 50 extending therethrough. Central opening 50 receives end 44 of one of wires 38 and 40 so that end 44 frictionally is retained within central opening 50 of base portion 48. Formed within central opening 50 at an upper end 52 is a stopper (not shown) which permits end 44 of resilient wire 38 or 40 to freely move within central opening 50 but prevents end 44 from being removed from central opening 50 at upper end 52.

Connecting member 46 has an ear 54 extending from base portion 48, wherein ear 54 has an opening 56 which is sized to receive retaining pin 34 so that ear 54 frictionally engages and retains pin 34. As a result, ends 44 of wires 38 and 40 are secured to earmuff cup assemblies 14 and 16 by the intimate coupling between connector member 46 and retaining pin 34. It will now be understood that end 44 is free to slide within central opening 50 so that earmuff 14 and 16 may be slidably adjusted with respect to connecting band 12 so as to dispose them around the ears and resiliently against the head of a wearer. It being understood that any number of connecting bands 12 may be used in earmuff 10 of the present invention and the illustrated connecting band 12 is merely illustrates one type of connecting band 12 which may be used.

As best shown in FIG. 3, cushion 20 is generally formed of a plurality of thin sheets of flexible polyvinyl chloride or polyurethane, one of the sheets being vacuum formed 60 and filled with a foam 62 or a liquid, then thermally bonded to a second sheet 64, after which the trim is cut off. It being understood that other types of cushions 20 may be used with the earmuff cups 14 and 16 of the present invention. The shape of cushion 20 may be cylindrical, round, or rectangular to fit the generally matching earmuff cup 14 and 16 design in a reasonable manner. Cushion 20 is quite flexible and may also be made to a shape requiring deformation to fit earmuff cup assemblies 14 and 16. Cushion 20 defines a central opening 21 which generally has a shape which matches the shape of cushion 20. Opening 21 is generally aligned with the internal portions of an ear, as shown and described in reference to FIG. 4, when earmuff device 10 is worn and covers the ear.

One exemplary and preferred cushion 20 is disclosed in commonly assigned U.S. Pat. No. 5,420,381 to Gardner Jr. et al., which is hereby incorporated in its entirety.

Optional earmuff cup liner 22 generally comprises an open cell foam or other material containing open pores of size and shape to absorb high frequency sound of about 1000 to about 8000 Hertz. Typically, polyurethane open-celled acoustical foam is used because of its low cost and low density. In the illustrated embodiment, earmuff cup liner 22 defines a central opening 25 similar to opening 21 defined by cushion 20. Preferably, opening 21 has an identical or similar diameter as opening 25. When earmuff cup liner 22 is inserted and secured within earmuff device 10, openings 21 and 25 are aligned so that the internal portions of the ear may be viewed through openings 21 and 25. It is within the scope of the present invention that the surface area of earmuff cup liner 22 may be expanded so long as opening 25 formed within earmuff cup liner 22 permits an individual to view opening 21 of cushion 20 by looking through cup shaped portion 24 and opening 21.

In accordance with the present invention, a portion of or all of cup shaped portion 24 is transparent or translucent so that compliance with dual hearing protection requirements can easily be ascertained by simply viewing the ear of a wearer through the transparent or translucent portion of cup shaped portion 24. Referring to FIGS. 1–4 which illustrates a first embodiment of the present invention in which the entire or substantially the entire cup shaped portion 24 is transparent or translucent so that an object disposed within the earmuff device 10 is visually perceivable from the outside of cup shaped portion 24. In this embodiment, cup shaped portion 24 is formed of either transparent, rigid material or a translucent, rigid material that has sufficient translucency so that an object inserted within an ear is visually perceivable through cup shaped portion 24 ("sufficient translucency"). In a preferred embodiment, cup shaped portion 24 is formed transparent, rigid polyvinyl chloride or acrylonitrile butadiene styrene (ABS) or translucent, rigid polyvinyl chloride or acrylonitrile butadiene styrene (ABS) having sufficient translucency as previously described hereinbefore.

The precise color of cup shaped portion 24 is not critical to the practice of the present invention so long as the object inserted into an ear, e.g. an inserted earplug or the like, is visually perceivable through cup shaped portion 24. It being understood that the fine details of this object need not be discernable by the observer so long as the object itself is capable of being visually perceived. Thus, contrasting colors between the color of cup shaped portion 24 and the object inserted into the ear will increase the likelihood that the object can be easily discernable through cup shaped portion 24.

Figure 4:
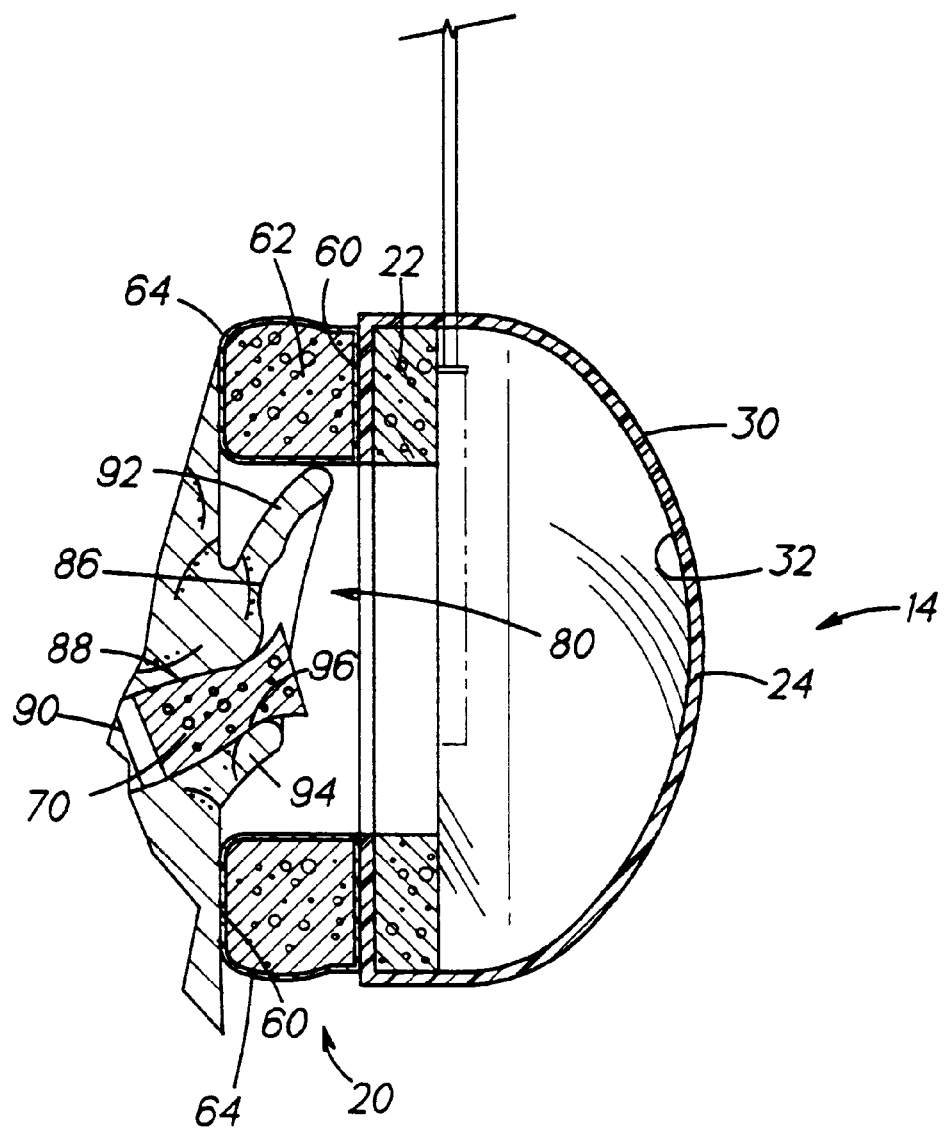
FIG. 4 is a cross section through an exemplary earmuff cup of the present invention showing an earplug disposed within the earmuff cup and inserted within a wearer's ear.

FIG. 4 illustrates earmuff 10 of the present invention being simultaneously worn with an earplug 70 on an ear 80 of the wearer. Cup shaped portion 24 covers ear 80 and rests on cushion 20 that presses against the head 82 to provide an acoustic seal, restricting the entrance of sound into large cavity 84. As is known, ear 80 is generally formed of a concha 86, ear canal 88, and eardrum 90. The external portion of ear 80 comprises a pinna 92 and the tragus 94 has an irregular shape that differs widely from one person to another and generally has at least one valley 96. Earplug 70 is inserted into ear canal 88 of the wearer to act as a first hearing protective device. As previously explained, when a dual hearing protective device is required to be worn, the wearer must also wear a second hearing protective device which in this case is earmuff device 10 of the present invention. Because in this embodiment, the entire or substantially entire cup shaped portion 24 is transparent or of sufficient translucency, earplug 70 is easily visually perceivable through cup shaped portion 24. This greatly improves and makes much easier the entire compliance check process so that a supervisor or other individual need simply to observe ear 80 of the wearer to see if earplug 70 is properly inserted as required in a dual hearing protection environment.

Figure 5:
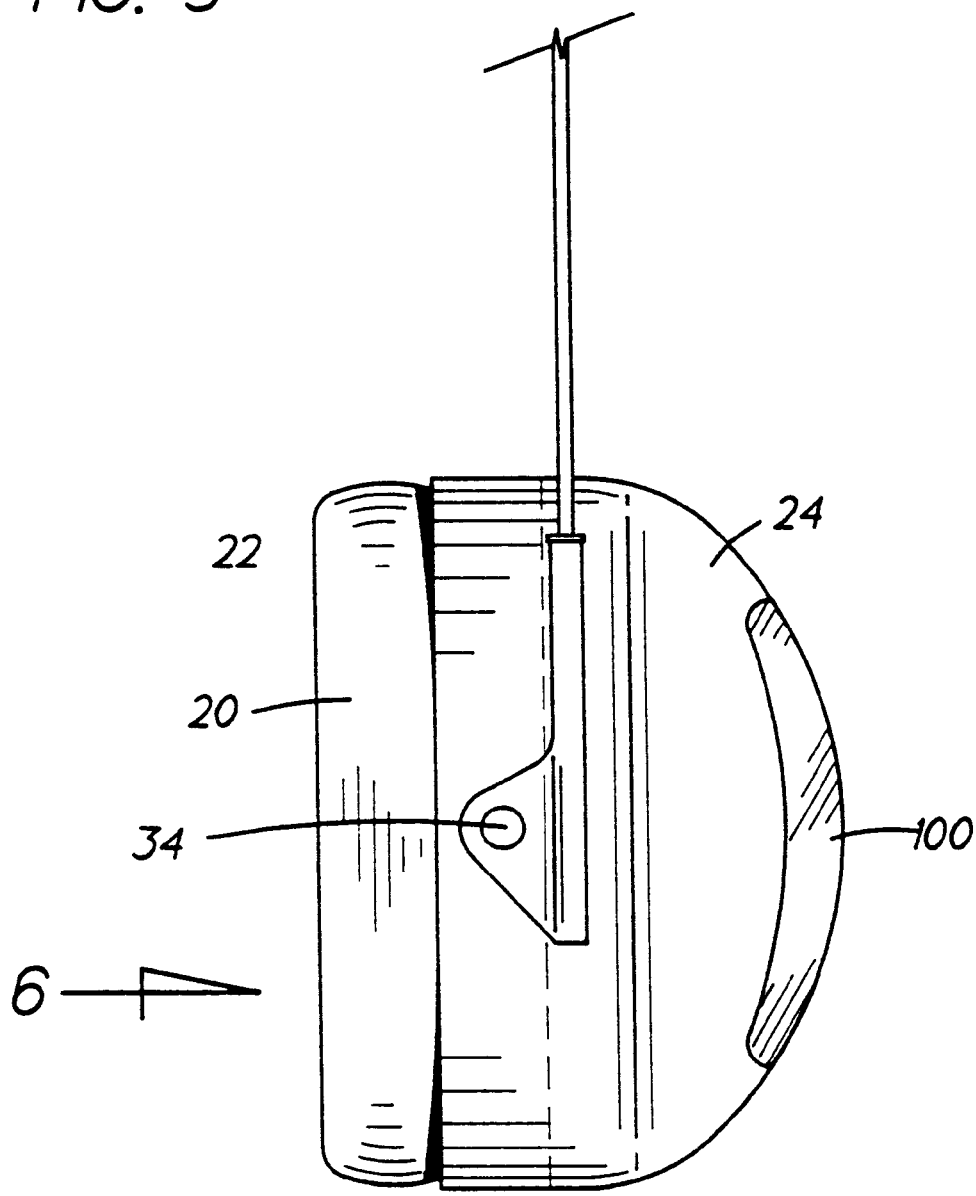
FIG. 5 is a side elevation view of an acoustic earmuff cup according to a second embodiment of the present invention.
Figure 6:
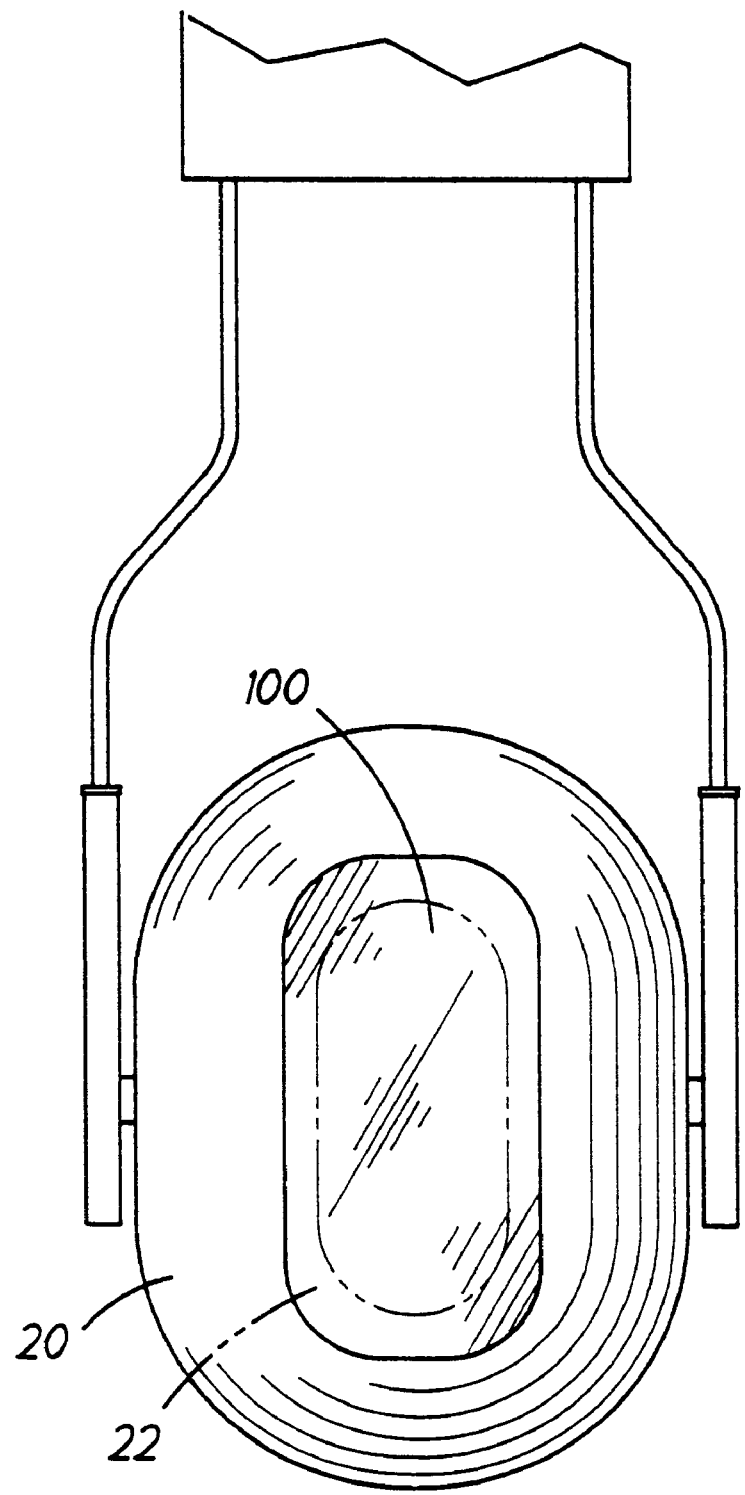
FIG. 6 is a front elevation view of the exemplary earmuff cup of FIG. 5 looking in the direction of arrow 6 in FIG. 5.

FIGS. 5 and 6 illustrate a second embodiment of the present invention. In this second embodiment, cup shaped portion 24 includes a window 100 formed therein, wherein window 100 is formed of a transparent material or of a material having sufficient translucency so that an object, e.g., earplug 70 (FIG. 4), inserted into ear 80 (FIG. 4) is visually perceivable through window 100. Accordingly, window 100 is sized so that an object inserted into ear 80 is capable of being visually perceived through window 100 when earmuff 10 is worn and covers ear 80. In the exemplary embodiment shown in FIGS. 5 and 6, window 100 is generally oval in shape; however, window 100 may have a variety of shapes so long as the object inserted in ear canal 88 (FIG. 4) is visually perceivable through window 100. Accordingly, window 100 is positioned within cup shaped portion 24 so that ear 80 and more particularly concha 86 and ear canal 88 (FIG. 4) are capable of being viewed therethrough.

FIG. 7 is a perspective view of an earmuff according to a second embodiment of the present invention and generally is indicated at 200. Earmuff 200 broadly comprises a generally U-shaped, resilient connecting band 202 and a pair of acoustic earmuff cup assemblies 204, 206 connected to opposite ends of connecting band 202. Earmuff cup assemblies 204, 206 each include rigid earcup 208, foam cushion 210, and optionally earmuff cup liner (not shown). Rigid cup 208 includes a cup shaped portion. Foam cushion 210 is formed of suitable materials including those disclosed in U.S. Pat. No. 5,420,381 and the earmuff cup liner generally comprises an open cell foam or other material containing open pores.

In the exemplary embodiment shown, connecting band 202 connects to earmuff cup assemblies 204, 206 by posts 216 which are integrally formed with connecting band 202 and inwardly extend towards one another. Each of posts 216 includes a head portion with an annular lip (not shown) which is received within an opening 218 formed in rigid cup 208. Preferably, opening 218 is centrally located within cup shaped portion of rigid cup 208. Post 216 engages rigid cup 208 in a snap-fit manner and is easily removed therefrom. The illustrated earmuff 200 with the illustrated cup shaped portion is described in general detail in commonly assigned U.S. Pat. No. 5,500,958 to Falco and which is incorporated herein by reference in its entirety. In accordance with the present invention, either the entire or a section of cup shaped portion of rigid cup 208 is transparent or translucent so that an object inserted into the ear is visually perceivable from the outside of the cup shaped portion. In a preferred embodiment, the cup shaped portion is formed of a transparent or translucent material selected from the group consisting of polyvinyl chloride or acrylonitrile butadiene styrene (ABS). In the illustrated embodiment, the cup shaped portion is formed entirely of either a transparent or translucent material; however, it will be appreciated that the cup shaped portion may include only a window (not shown) which is formed of a transparent or translucent material so long as the window permits an object disposed within the ear to be visually perceivable through the window.

While preferred embodiments have been shown and described, various modifications and substitutions may be made thereto without departing from the spirit and scope of this invention. Accordingly, it is understood that the present invention has been described by way of illustrations and not limitation. For example, the illustrated earmuffs are merely exemplary in nature and it is within the scope of the present invention that any earmuff having a rigid earcup may be manufactured so that either the entire rigid cup or a portion of the rigid cup is formed of a transparent or sufficiently translucent material so that an object inserted into or disposed around the user's ear is visually perceivable through the rigid cup.

What is claimed is:

1. An acoustic earmuff device comprising:
   a flexible connecting band having opposing first and second ends; and
   a pair of earmuff cup assemblies connected to the opposing first and second ends of the connecting band and encompassing a wearer's ear to attenuate noise, wherein each earmuff cup assembly includes:

a rigid cup having at least a portion which is transparent or translucent so that an object inserted into the ear of the wearer is visually perceivable through the rigid cup, an earmuff cushion secured to the rigid cup, the earmuff cushion being for contact with the side of the wearer's head, and an earmuff cup liner disposed about a first peripheral rim surface of the rigid cup, the earmuff cushion being disposed around an opposing second peripheral rim surface of the rigid cup.

2. The acoustic earmuff device of claim 1, wherein the rigid cup is formed of transparent polyvinyl chloride or acrylonitrile butadiene styrene.

3. The acoustic earmuff device of claim 1, wherein the rigid cup is formed of translucent polyvinyl chloride or acrylonitrile butadiene styrene.

4. The acoustic earmuff device of claim 1, wherein the at least a portion of the rigid cup comprises a window formed therein.

5. The acoustic earmuff device of claim 4, wherein the window is centrally located in the rigid cup.

6. The acoustic earmuff device of claim 1, wherein the earmuff cup liner and earmuff cushion are generally oval shaped with openings formed therein, the openings being axially aligned so that the ear of the wearer is at least partially visible through the rigid cup.

7. The acoustic earmuff device of claim 1, wherein the entire rigid cup is formed of a transparent or translucent material.

8. The acoustic earmuff device of claim 1, wherein the rigid cup is clear in color.

9. The earmuff device of claim 1, wherein the connecting band comprises:

a pair of generally parallel disposed first and second resilient wires held in substantially parallel alignment by a strip formed of a flexible material.

10. The earmuff device of claim 1, wherein the connecting band comprises:

a generally U-shaped band having posts integrally formed at each end, the posts inwardly extending from the U-shaped band toward one another, the U-shaped band being removably retained to the rigid cup in a snap-fit manner by disposing the posts within openings formed in the rigid cup so that the posts snap-fit to the rigid cup.

11. An earmuff device, comprising:

a connecting band having opposing first and second ends; and a pair of earmuff cup assemblies connected to the opposing first and second ends of the connecting band and encompassing a wearer's ear to attenuate noise, wherein each earmuff cup assembly includes:

a rigid cup having at least a portion which is transparent or translucent so that an object inserted into an ear of a wearer is visually perceivable through the rigid cup, the rigid cup being formed of a polymeric material; and an earmuff cushion secured to the rigid cup, the earmuff cushion being for contact with the side of the wearer's head.

12. The earmuff device of claim 11, wherein the rigid cup is formed of transparent polyvinyl chloride or acrylonitrile butadiene styrene.

13. The earmuff device of claim 11, wherein the cup is formed of translucent polyvinyl chloride or acrylonitrile butadiene styrene.

14. The earmuff device cup of claim 11, wherein the at least a portion of the rigid cup comprises a window formed in the earmuff cup.

15. A dual hearing protective assembly comprising:

a pair of earplugs for insertion into ears of a wearer; and an acoustic earmuff device including:

a flexible connecting band having opposing first and second ends;

a pair of earmuffs connected to the opposing first and second ends of the connecting band and encompassing the wearer's ear to attenuate noise, wherein each earmuff includes a rigid cup having at least a portion which is transparent or translucent so that the earplug inserted within the ear of the wearer is visually perceivable through the rigid cup, the earmuff further including an earmuff cushion secured to the rigid cup, the earmuff cushion being for contact with the side of the wearer's head.

16. The dual hearing protective assembly of claim 15, wherein the rigid cup is formed of transparent polyvinyl chloride or acrylonitrile butadiene styrene.

17. The dual hearing protective assembly of claim 15, wherein the rigid cup is formed of translucent polyvinyl chloride or acrylonitrile butadiene styrene.

18. The dual hearing protective assembly of claim 15, wherein the at least a portion of the rigid cup comprises a window formed in the rigid cup.

* * * * *

UNITED STATES PATENT AND TRADEMARK OFFICE
CERTIFICATE OF CORRECTION

PATENT NO. : 6,151,717
DATED : November 28, 2000
INVENTOR(S) : Jim Hall et al.

It is certified that error appears in the above-identified patent and that said Letters Patent is hereby corrected as shown below:

Column 5,
Line 62, after "into" delete "car" and insert therefor -- ear --.

Column 8,
Line 6, after "an" (2nd occurrence) delete "car" and insert therefor -- ear --.

Signed and Sealed this

Thirty-first Day of December, 2002

JAMES E. ROGAN
*Director of the United States Patent and Trademark Office*